United States Patent
Endo et al.

(10) Patent No.: US 9,939,498 B2
(45) Date of Patent: Apr. 10, 2018

(54) MAGNETIC SENSOR

(71) Applicant: ALPS ELECTRIC CO., LTD., Ota-ku, Tokyo (JP)

(72) Inventors: Hiroaki Endo, Tokyo (JP); Hideto Ando, Tokyo (JP); Sumihito Morita, Tokyo (JP); Takafumi Noguchi, Tokyo (JP)

(73) Assignee: ALPS ELECTRIC CO., LTD., Tokyo (JP)

( * ) Notice: Subject to any disclaimer, the term of this patent is extended or adjusted under 35 U.S.C. 154(b) by 97 days.

(21) Appl. No.: 15/093,905

(22) Filed: Apr. 8, 2016

(65) Prior Publication Data

US 2016/0313409 A1    Oct. 27, 2016

(30) Foreign Application Priority Data

Apr. 22, 2015   (JP) .................. 2015-087867

(51) Int. Cl.
*G01B 7/14*  (2006.01)
*G01R 33/09*  (2006.01)
*G01N 27/90*  (2006.01)

(52) U.S. Cl.
CPC .......... *G01R 33/09* (2013.01); *G01N 27/902* (2013.01); *G01N 27/9033* (2013.01)

(58) Field of Classification Search
CPC .... G01R 33/09; G01R 33/093; G01R 15/207; G01D 5/145; G01D 5/147; G01B 7/30; G01B 7/003; G01N 27/9033; G01N 27/902; G01N 27/9013; G01N 27/904; G01N 27/223; G01N 27/82; G01N 27/9093
See application file for complete search history.

(56) References Cited

U.S. PATENT DOCUMENTS

| | | | | |
|---|---|---|---|---|
| 6,462,541 B1 * | 10/2002 | Wang | ............... | B82Y 25/00 324/252 |
| 8,461,834 B2 * | 6/2013 | Honkura | ............ | G01R 33/0052 257/427 |
| 2004/0150397 A1 * | 8/2004 | Kuroe | ............... | G01R 33/02 324/249 |
| 2005/0179431 A1 * | 8/2005 | Muramatsu | ............ | G01R 33/02 324/250 |
| 2012/0200292 A1 | 8/2012 | Sugihara et al. | | |
| 2015/0192432 A1 * | 7/2015 | Noguchi | ............... | G01R 33/09 324/207.2 |

* cited by examiner

*Primary Examiner* — Thang Le

(74) *Attorney, Agent, or Firm* — Hunton & Williams LLP

(57) ABSTRACT

A magnetic sensor includes a substrate, magnetoresistive effect elements arranged on a surface of the substrate, a first wiring line arranged on a surface of the substrate, an insulation layer configured to cover the magnetoresistive effect elements and the first wiring line, a soft magnetic body arranged on the insulation layer, and a second wiring line arranged on the insulation layer, wherein the magnetoresistive effect elements each extend in a first direction and are arranged while being separated from each other in a second direction orthogonal to the first direction in a case of viewing in plan the substrate, the soft magnetic body includes a first direction extension portion that extends in the first direction, and when viewed in plan, the first direction extension portion is arranged between the magnetoresistive effect elements, and the second wiring line is connected to the first wiring line.

8 Claims, 3 Drawing Sheets

100

MAGNETIC SENSOR

CLAIM OF PRIORITY

This application contains subject matter related to and claims the benefit of Japanese Patent Application No. 2015-087867 filed on Apr. 22, 2015, the entire contents of which is incorporated herein by reference.

BACKGROUND OF THE DISCLOSURE

1. Field of the Disclosure

The present disclosure relates to a magnetic sensor.

2. Description of the Related Art

For example, International Publication No. WO2011/068146 discloses a magnetic sensor that uses a magnetoresistive effect element capable of simply and adequately detecting a vertical magnetic-field component. The magnetic sensor includes a magnetoresistive effect element, which is formed by laminating a magnetic layer and a non-magnetic layer on a substrate and which produces a magnetoresistive effect, and a soft magnetic body, which converts an external vertical magnetic-field component into magnetic-field components in a horizontal direction, which applies the magnetic-field components converted into the horizontal direction to the magnetoresistive effect element, and which is not in contact with the magnetoresistive effect element. According to the magnetic sensor, it is thought that it is possible to produce, with a simple configuration, a magnetic sensor that uses the magnetoresistive effect element capable of detecting the vertical magnetic-field component, it is possible to inexpensively produce the magnetic sensor, and it is possible to accelerate miniaturization.

In the magnetic sensor described in International Publication No. WO2011/068146, the external vertical magnetic field is converted into the magnetic-field components in the horizontal direction by using the soft magnetic substance, and this is applied to the magnetoresistive effect element, thereby detecting the vertical magnetic field. Here, the converted magnetic-field components in the horizontal direction are separated into two components in a first sidewise direction in a case of viewing in plan the soft magnetic body and in a second sidewise direction opposite thereto. Therefore, an element such as, for example, a giant magneto resistive effect (GMR) element, which detects, based on a change in a resistance value, a difference between magnetization directions of a fixed magnetic layer and a free magnetization layer is used. Accordingly, depending on which of the first sidewise direction and the second sidewise direction the relevant element is placed in a case of viewing in plan the soft magnetic body, it becomes possible to configure so that a change in the resistance value is output in an opposite direction with respect to the same external magnetic-field input. In other words, it becomes possible to very easily configure a bridge circuit by combining an element arranged in the first sidewise direction and an element arranged in the second sidewise direction. When arranging the elements in only one of the first sidewise direction and the second sidewise direction of the soft magnetic body, one of two magnetic fields is not used, and an element area is wasted. Accordingly, the case is not desirable in view of a detection sensitivity. Therefore, it is desirable that the elements are used while being arranged in both the first sidewise direction and the second sidewise direction of the soft magnetic body.

However, in, for example, a case of intending to reduce the resistance values of the magnetoresistive effect elements, it becomes necessary to connect the magnetoresistive effect elements in parallel. In addition, in such a case, depending on conditions, it may become difficult to adequately wire the magnetoresistive effect elements while satisfying arrangement conditions of the magnetoresistive effect elements and the soft magnetic body.

These and other drawbacks exist.

SUMMARY OF THE DISCLOSURE

Embodiments of the present disclosure provide a technology for increasing the degree of freedom of a wiring layout of magnetoresistive effect elements, for reducing an element area, and for eventually enabling a cost to be reduced even in a case where there is a restriction in a relative arrangement relationship between the magnetoresistive effect elements and a soft magnetic body, as in the case of sensing a vertical magnetic field by using the soft magnetic body.

In order to solve the above-mentioned problem, in a first embodiment, a magnetic sensor includes a substrate, magnetoresistive effect elements arranged on a surface of the substrate, a first wiring line arranged on a surface of the substrate, an insulation layer configured to cover the magnetoresistive effect elements and the first wiring line, a soft magnetic body arranged on the insulation layer, and a second wiring line arranged on the insulation layer, wherein in a case where it is assumed that two directions, orthogonal to each other in a case of viewing in plan the substrate, are a first direction and a second direction, the magnetoresistive effect elements each extend in the first direction and are arranged while being separated from each other in the second direction, the soft magnetic body includes a first direction extension portion configured to extend in the first direction, the first direction extension portion is arranged, in a case of being viewed in plan, between the magnetoresistive effect elements arranged while being separated from each other in the second direction, and the second wiring line is connected to the first wiring line via a through-hole formed in the insulation layer.

The magnetoresistive effect elements may be arranged in the vicinities of two end portions in the second direction of the first direction extension portion in a case of being viewed in plan. The first wiring line may be connected to an end portion in the first direction of each of the magnetoresistive effect elements, and the second wiring line may be arranged in the vicinity of a soft magnetic body arrangement area in which the soft magnetic body is arranged.

The first wiring line may include a comb-shaped wiring line having a comb-shaped pattern in a case of being viewed in plan and a straight wiring line having a line pattern in a case of being viewed in plan, the straight wiring line may be arranged between comb teeth of the comb-shaped wiring line, and the second wiring line may connect the straight wiring lines while lying astride the comb teeth of the comb-shaped wiring line. In this case, the magnetoresistive effect elements may be connected in parallel by using the comb-shaped wiring line, the straight wiring lines, and the second wiring line. In addition, the comb-shaped wiring line, the magnetoresistive effect elements, the straight wiring lines, and the second wiring line may be connected, thereby enabling a bridge circuit to be configured.

The soft magnetic body may include a second direction extension portion configured to extend in the second direction, two end portions in the first direction of the first direction extension portion may be short-circuited by the second direction extension portion, and a closed magnetic-field path may be configured by the first direction extension portion and the second direction extension portion. The soft magnetic body may convert an external vertical magnetic-field component into a magnetic-field component in a horizontal direction, and the magnetic-field component converted into the horizontal direction may be applied to the magnetoresistive effect elements.

Note that the above-mentioned summary of the invention does not correspond to a recitation of all necessary features of the present invention. In addition, a subcombination of these feature groups may be an invention.

DETAILED DESCRIPTION OF THE DISCLOSURE

While hereinafter the present invention will be described through an example embodiment of the disclosure, the following embodiment does not limit claimed inventions. In addition, all of combinations of features described in the embodiment are not always essential to solutions of the invention.

The following description is intended to convey a thorough understanding of the embodiments described by providing a number of specific embodiments and details involving a magnetic sensor. It should be appreciated, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments, depending on specific design and other needs.

Figure 1:
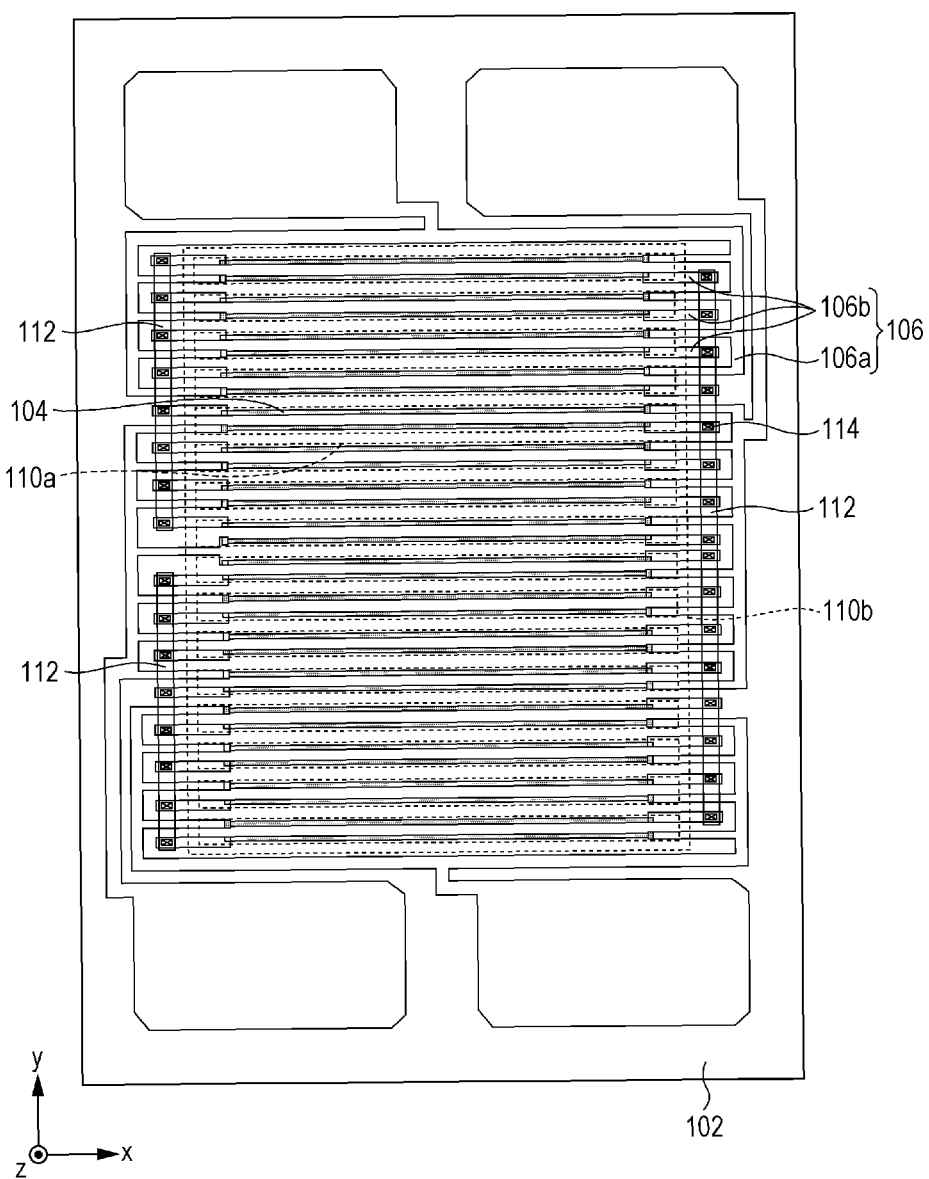
FIG. 1 is a plan view of a magnetic sensor.
Figure 2:
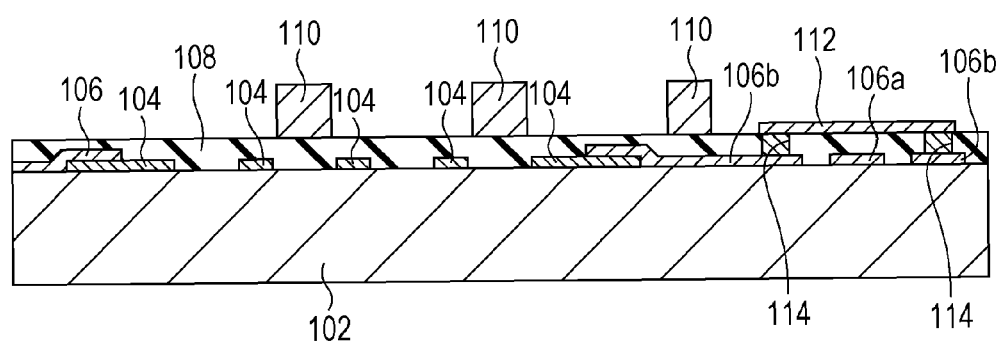
FIG. 2 is a partial cross-sectional view of the magnetic sensor.

FIG. 1 illustrates a plan view of a magnetic sensor 100. FIG. 2 is a partial cross-sectional view of the magnetic sensor 100. FIG. 2 does not illustrate an accurate cross-section in a specific location in FIG. 1. For convenience of explanation, a portion is conceptualized and illustrated. Note that, in FIG. 1, it is assumed that a first direction and a second direction, which are orthogonal to each other in a case of viewing in plan a substrate 102, are an x direction and a y direction, respectively, and a direction orthogonal to both the x direction and the y direction is a z direction.

The magnetic sensor 100 may include the substrate 102, magnetoresistive effect elements 104, first wiring lines 106, an insulation layer 108, a soft magnetic body 110, and second wiring lines 112.

The substrate 102 may be formed of a non-magnetic material. As long as the substrate 102 is the non-magnetic material, the type of material thereof or the like does not matter. As the substrate 102, a ceramic substrate, a semiconductor substrate, and so forth may be exemplified. The magnetoresistive effect elements 104 may be formed on the surface of the substrate 102, and the first wiring lines 106 may be formed on the surface of the substrate 102. The insulation layer 108 covers the magnetoresistive effect elements 104 and the first wiring lines 106, and the soft magnetic body 110 is arranged on the insulation layer 108.

The second wiring lines 112 may be formed on the insulation layer 108. The first wiring lines 106 each may include a comb-shaped wiring line 106a, which has a comb-shaped pattern in a case of being viewed in plan, and straight wiring lines 106b, which each have a line pattern in a case of being viewed in plan. The soft magnetic body 110 may include first direction extension portions 110a, which extend in the first direction (the x direction), and second direction extension portions 110b, which extend in the second direction (the y direction).

As each of the magnetoresistive effect elements 104, an element, whose resistance value changes in response to a magnetic field and whose examples include a giant magneto resistive effect (GMR) element, a tunnel magneto resistance effect (TMR) element, and so forth, may be exemplified. In a case where the magnetoresistive effect elements 104 are the GMR elements, an antiferromagnetic layer, a fixed magnetic layer, a non-magnetic layer, and a free magnetic layer may be laminated in order from the bottom, thereby film-forming each of the magnetoresistive effect elements 104, and the surface of the free magnetic layer is covered by a protective layer. The magnetoresistive effect elements 104 are film-formed by, for example, sputtering.

The antiferromagnetic layer may be formed of an antiferromagnetic material such as an iridium-manganese (IrMn) alloy. The fixed magnetic layer may be formed of a soft magnetic material such as a cobalt-iron (CoFe) alloy. The fixed magnetic layer may be formed by using a laminated ferrimagnetic structure. The non-magnetic layer is copper (Cu) or the like. The free magnetic layer may be formed of a soft magnetic material such as a nickel-iron (NiFe) alloy. The protective layer may be tantalum (Ta) or the like. The laminated structure of each of the magnetoresistive effect elements may be another laminated structure.

Figure 3:
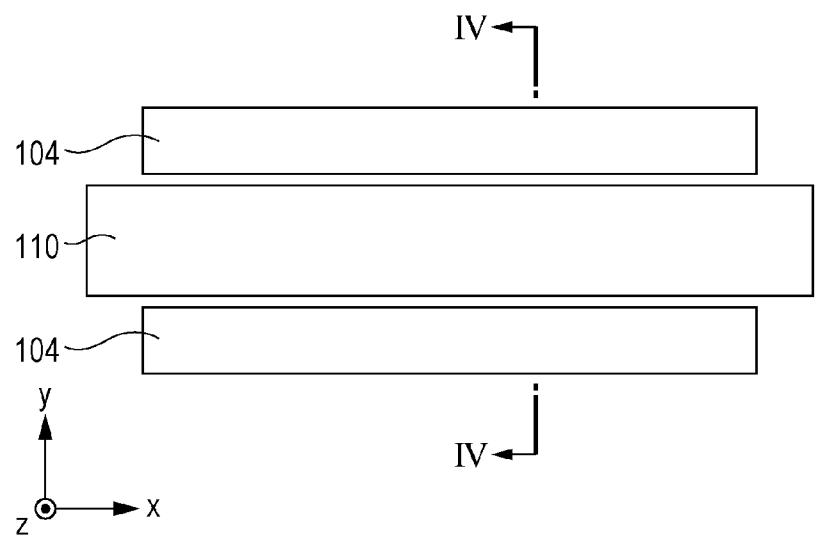
FIG. 3 is a plan view illustrating a magnified portion of the magnetic sensor.
Figure 4:
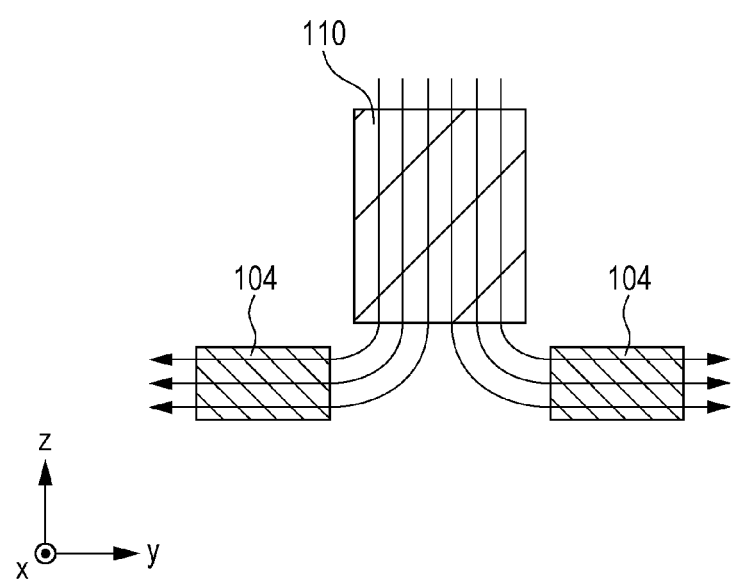
FIG. 4 illustrates a cross-sectional view taken along a line IV-IV.

The magnetoresistive effect elements 104 may extend in the first direction (the x direction) and may be arranged in parallel while being separated from each other in the second direction (the y direction). Each of the first direction extension portions 110a of the soft magnetic body 110 may be arranged between the corresponding two magnetoresistive effect elements 104 out of the magnetoresistive effect elements 104 in the second direction (the y direction). In addition, the corresponding two magnetoresistive effect elements 104 out of the magnetoresistive effect elements 104 may be formed in the vicinities of respective two end portions of the corresponding one of the first direction extension portions 110a in the second direction. Each of FIG. 3 and FIG. 4 is a diagram illustrating this in detail and is a diagram magnifying one of the first direction extension portions 110a. The soft magnetic body 110 may convert, into the second direction (the y direction), a magnetic field in a vertical direction (the z direction) in a case of being viewed in plan. The corresponding two magnetoresistive effect elements 104 out of the magnetoresistive effect elements 104 may be formed in the vicinities of respective two end portions of the soft magnetic body 110 (the corresponding one of the first direction extension portions 110a) in the second direction. Therefore, it is possible to effectively capture the magnetic field in the vertical direction with no loss. At this time, respective resistance value changes, whose directions are opposite to each other, of the corresponding two magnetoresistive effect elements 104 arranged in the vicinities of respective two end portions of the corresponding one of the first direction extension portions 110a are output in response to the magnetic field in the vertical direction (the z direction).

The first wiring lines 106 may be connected to end portions of the magnetoresistive effect elements 104 in the first direction (the x direction). Here, the magnetoresistive effect elements 104 may be arranged in the y direction, in which respective resistance value changes, whose directions are opposite to each other, of the corresponding two magnetoresistive effect elements 104 out of the magnetoresistive effect elements 104 are output in response to the magnetic field in the vertical direction (the z direction) and in which the corresponding two magnetoresistive effect elements 104 may be alternately arranged in the y direction. The corresponding two magnetoresistive effect elements 104 whose resistance value changes are equal in direction may be electrically connected in parallel, thereby enabling an obtained output to be increased, and furthermore, by using the magnetoresistive effect elements 104 whose resistance value changes are equal in direction with respect to one of the two directions and which are electrically connected in parallel and the magnetoresistive effect elements 104 whose resistance value changes are equal in direction with respect to the other direction and which are electrically connected in parallel, a bridge circuit may be configured, thereby enabling the influence of a disturbance magnetic field to be decreased and enabling a detection sensitivity to be increased. However, the magnetoresistive effect elements 104 may be arranged in the y direction, in which respective resistance value changes, whose directions are opposite to each other, of the corresponding two magnetoresistive effect elements 104 out of the magnetoresistive effect elements 104 are output in response to the magnetic field in the vertical direction (the z direction) and in which the corresponding two magnetoresistive effect elements 104 may be alternately arranged in the y direction. Therefore, in order to electrically connect the magnetoresistive effect elements 104 whose resistance value changes are equal in direction, a wiring line becomes complicated, the routing of a wiring line on the surface of the substrate 102 becomes long, and a wiring line area becomes wide. Accordingly, there is a problem that it is difficult to reduce the size of an entire magnetic sensor.

In order to solve such a problem as described above, in the magnetic sensor 100 of the present embodiment, the first wiring lines 106 do not exist in an area in which the magnetoresistive effect elements 104 are formed, and the first wiring lines 106 may be formed only in the vicinities of areas in which the magnetoresistive effect elements 104 are formed. Therefore, it is possible to increase the density of the magnetoresistive effect elements 104 and to reduce the size of the entire magnetic sensor. As a result, it is possible to improve productivity and to reduce a cost.

In addition, the second wiring lines 112 may be formed in the vicinity of a soft magnetic body arrangement area in which the soft magnetic body 110 is arranged, and the second wiring lines 112 may be connected to the first wiring lines 106 via through-holes 114 formed in the insulation layer 108. Since being formed in a layer different from that of the first wiring lines 106, the second wiring lines 112 are able to be formed astride the first wiring lines 106 while maintaining an insulation property. As a result, the routing of a wiring line on the surface of the substrate 102 becomes short, it is possible to reduce a wiring line area, and it is possible to reduce the size of the entire magnetic sensor. Furthermore, it is possible to increase the degree of freedom of wiring design.

Each of the straight wiring lines 106b of the first wiring lines 106 may be formed between the corresponding comb teeth of the corresponding one of the comb-shaped wiring lines 106a, and the second wiring lines 112 may each connect the straight wiring lines 106b while lying astride the corresponding comb teeth of the comb-shaped wiring lines 106a. By using the comb-shaped wiring lines 106a, the magnetoresistive effect elements 104 may be easily connected in parallel. In addition, each of the straight wiring lines 106b may be formed between the corresponding comb teeth of the corresponding one of the comb-shaped wiring lines 106a, and the straight wiring lines 106b may be connected by using the second wiring lines 112. Accordingly, the parallel connection of the magnetoresistive effect elements 104 may be realized while satisfying a restriction on the arrangement of the soft magnetic body 110 and the magnetoresistive effect elements 104. In addition, by connecting the comb-shaped wiring lines 106a, the magnetoresistive effect elements 104, the straight wiring lines 106b, and the second wiring lines 112, the bridge circuit may be configured.

Two end portions of each of the first direction extension portions 110a of the soft magnetic body 110 in the first direction may be short-circuited by the second direction extension portions 110b, and a closed magnetic-field path may be configured by the first direction extension portions 110a and the second direction extension portions 110b. By providing the second direction extension portions 110b of the soft magnetic body 110, it is possible to reduce the influence of an external magnetic field from a lateral direction (the x direction or the y direction).

According to the magnetic sensor 100 of the present embodiment, even in a case where there is a restriction in a relative arrangement relationship between the magnetoresistive effect elements 104 and the soft magnetic body 110, it is possible to increase the degree of freedom of a wiring layout of the magnetoresistive effect elements 104 and, it is possible to reduce an element area. As a result, it is possible to reduce a cost.

While, as above, the present invention is described by using the embodiment, the technical scope of the present invention is not limited to a scope described in the above-mentioned embodiment. It is obvious to those skilled in the art that various alterations or modifications may be added to the above-mentioned embodiment. It is clear from the description of the scope of the appended claims that an embodiment to which such alterations or modifications are added is included in the technical scope of the present invention.

Accordingly, the embodiments of the present inventions are not to be limited in scope by the specific embodiments described herein. Further, although some of the embodiments of the present disclosure have been described herein in the context of a particular implementation in a particular environment for a particular purpose, those of ordinary skill in the art should recognize that its usefulness is not limited thereto and that the embodiments of the present inventions can be beneficially implemented in any number of environments for any number of purposes. Accordingly, the claims set forth below should be construed in view of the full breadth and spirit of the embodiments of the present inventions as disclosed herein. While the foregoing description includes many details and specificities, it is to be understood that these have been included for purposes of explanation only, and are not to be interpreted as limitations of the invention. Many modifications to the embodiments described above can be made without departing from the spirit and scope of the invention.

What is claimed is:

1. A magnetic sensor comprising:
a substrate;
magnetoresistive effect elements arranged on a surface of the substrate;
a first wiring line arranged on a surface of the substrate;
an insulation layer that covers the magnetoresistive effect elements and the first wiring line;
a soft magnetic body arranged on the insulation layer; and
a second wiring line arranged on the insulation layer, wherein
in a case where it is assumed that two directions, orthogonal to each other in a case of viewing in plan the substrate, are a first direction and a second direction,
the magnetoresistive effect elements each extend in the first direction and are arranged while being separated from each other in the second direction,
the soft magnetic body includes first direction extension portions that extend in the first direction, and in a case of being viewed in plan, a projection of each of the first direction extension portions on the plan view of the substrate is disposed between the magnetoresistive effect elements arranged while the first direction extension portions being separated from each other in the second direction, and the second wiring line is connected to the first wiring line via a through-hole formed in the insulation layer.

2. The magnetic sensor according to claim 1, wherein the magnetoresistive effect elements are arranged in the vicinities of two end portions in the second direction of the first direction extension portions in the plan view of the substrate.

3. The magnetic sensor according to claim 1, wherein the first wiring line is connected to an end portion in the first direction of each of the magnetoresistive effect elements, and the second wiring line is arranged in the vicinity of a soft magnetic body arrangement area in which the soft magnetic body is arranged.

4. The magnetic sensor according to claim 1, wherein the first wiring line includes a comb-shaped wiring line having a comb-shaped pattern in the plan view of the substrate and a straight wiring line having a line pattern in the plan view of the substrate,
the straight wiring line is arranged between comb teeth of the comb-shaped wiring line, and
the second wiring line connects the straight wiring lines while lying astride the comb teeth of the comb-shaped wiring line.

5. The magnetic sensor according to claim 4, wherein the magnetoresistive effect elements are connected in parallel by using the comb-shaped wiring line, the straight wiring lines, and the second wiring line.

6. The magnetic sensor according to claim 4, wherein the comb-shaped wiring line, the magnetoresistive effect elements, the straight wiring lines, and the second wiring line are connected, thereby configuring a bridge circuit.

7. The magnetic sensor according to claim 1, wherein the soft magnetic body includes second direction extension portions configured to extend in the second direction,
two end portions in the first direction of the first direction extension portions are short-circuited by the second direction extension portions, and
a closed magnetic-field path is configured by the first direction extension portions and the second direction extension portions.

8. The magnetic sensor according to claim 1, wherein the soft magnetic body converts an external vertical magnetic-field component into a magnetic-field component in a horizontal direction, and the magnetic-field component converted into the horizontal direction is applied to the magnetoresistive effect elements.

* * * * *